US012383323B2

(12) United States Patent
Livorsi et al.

(10) Patent No.: US 12,383,323 B2
(45) Date of Patent: Aug. 12, 2025

(54) INSERTER GUIDE AND DRIVER SYSTEM

(71) Applicant: DePuy Synthes Products, Inc., Raynham, MA (US)

(72) Inventors: Carl Livorsi, Raynham, MA (US); Francisco Amaral, Raynham, MA (US); Matthew Posluszny, Raynham, MA (US); Raymond Murphy, Raynham, MA (US); David Gerber, Raynham, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 75 days.

(21) Appl. No.: 18/106,878

(22) Filed: Feb. 7, 2023

(65) Prior Publication Data

US 2023/0263641 A1    Aug. 24, 2023

Related U.S. Application Data

(63) Continuation of application No. 16/550,853, filed on Aug. 26, 2019, now Pat. No. 11,602,442, which is a continuation of application No. 15/241,768, filed on Aug. 19, 2016, now Pat. No. 10,390,967.

(51) Int. Cl.
*A61B 17/88* (2006.01)
*A61F 2/46* (2006.01)
*A61B 17/90* (2006.01)
*A61F 2/30* (2006.01)

(52) U.S. Cl.
CPC ...... *A61B 17/8875* (2013.01); *A61B 17/8894* (2013.01); *A61F 2/4611* (2013.01); *A61B 17/90* (2021.08); *A61F 2002/30787* (2013.01); *A61F 2002/4627* (2013.01); *A61F 2002/4628* (2013.01); *A61F 2002/4687* (2013.01)

(58) Field of Classification Search
CPC ............................ B25G 1/063; A61B 17/8875
See application file for complete search history.

(56) References Cited

U.S. PATENT DOCUMENTS

| 6,830,574 B2 | 12/2004 | Heckele et al. |
| 9,173,750 B2 | 11/2015 | Weiman et al. |
| 2001/0021853 A1* | 9/2001 | Heckele ................. A61F 2/4611 606/104 |
| 2014/0018816 A1* | 1/2014 | Fenn .................... B25B 23/0035 606/104 |

* cited by examiner

*Primary Examiner* — Andrew Yang
(74) *Attorney, Agent, or Firm* — BakerHostetler

(57) ABSTRACT

Disclosed herein is a guide device and a driver, which allows for the preparation of an anatomic cavity for screw fixation of an implant or spacer, including the guidance for hole preparation, and guidance for insertion of screws, and or anchors, while selecting the amount of rigidity, and selecting the amount of visibility.

17 Claims, 19 Drawing Sheets

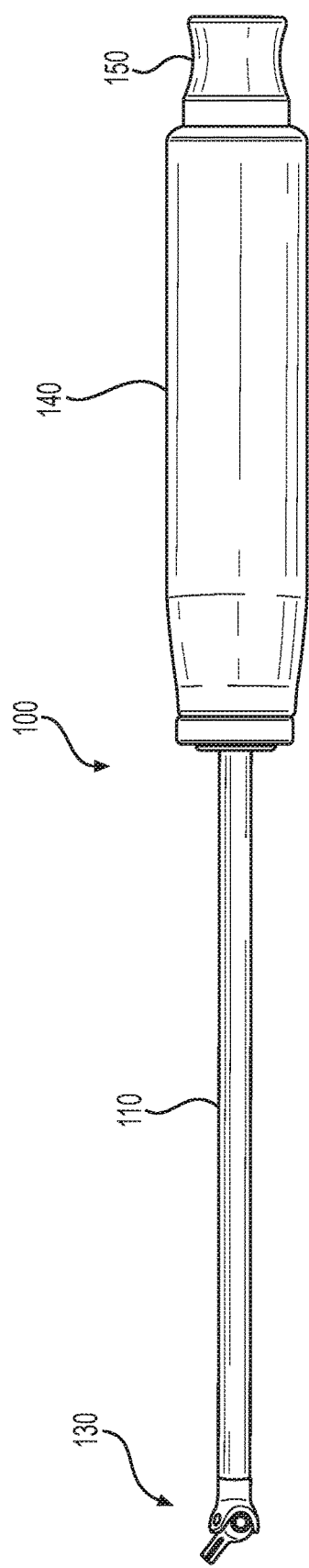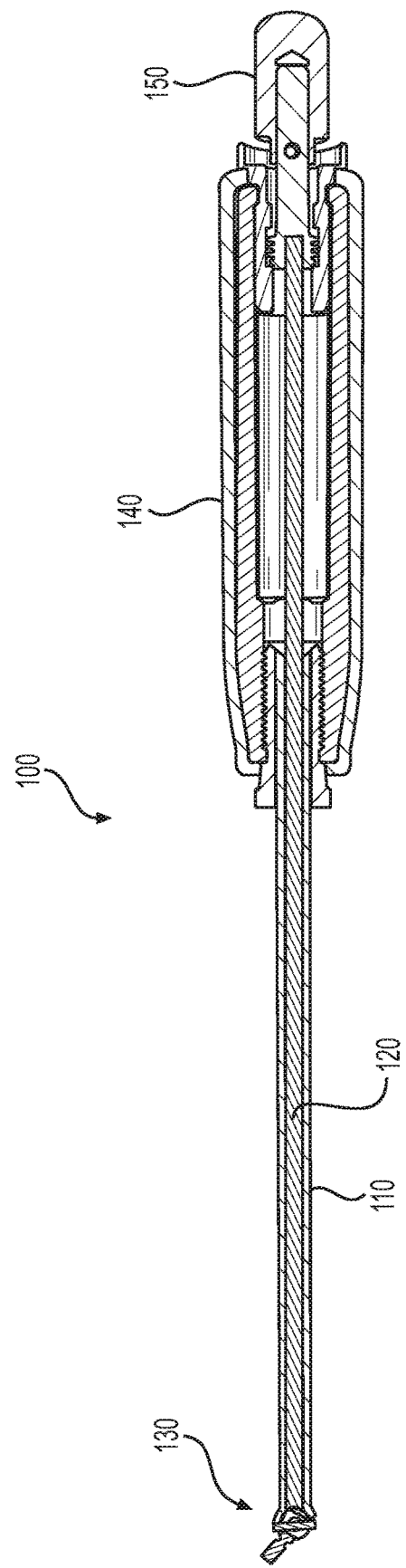

INSERTER GUIDE AND DRIVER SYSTEM

BACKGROUND

In procedures such as an anterior lumbar interbody fusion (ALIF), lateral lumbar interbody fusion (XLIF), and cervical spine surgery, for example, when a disc space has been cleared out, a metal, polymer, or bone implant/spacer is typically implanted between the two adjoining vertebrae. After these spacers or "cages" are inserted, surgeons often use metal screws, plates, and/or rods to further stabilize the spine. To insert the screws, a driver device having an articulating driver head may be used to deliver the screws to the spinal column and lock them and the spacer into place.

In many fixation procedures, particularly those around the cervical spine, the surgeon has a very limited surgical approach and an especially small soft tissue opening. Additionally, typical attempts at screw hole preparation and driving of the bone screw require two hands, one to hold the guide and one to prepare the hole/drive the bone screw. During the fixation procedure, including drill guidance for hole preparation, the straight-line approach of the driver/driver structure further limits visibility. Accordingly, it is needed in the art to have an inserted guide and driver that are minimally invasive and provide improved functionality while increasing visibility of both the surgical tools and treatment area.

SUMMARY

The present disclosure provides a driver for an inserter guide system. The driver may comprise a rotatable driver shaft. The driver may also comprise a rod disposed within the rotatable driver shaft, as well as a driver tip coupled to the rod at a rotatable and pivotable joint. The driver tip may include an interface extending therefrom adapted to engage a fastener. The driver may include a housing that receives the rotatable driver shaft at a distal end thereof. There may be a control element disposed at a proximal end of the housing. The control element may receive a proximal end of the rod within the housing, wherein actuation of the control element engages the proximal end of the rod, causing a distal end of the rod to frictionally engage the rotatable joint.

Also provided herein is an inserter guide system comprising an implant holder and guide device. The implant holder and guide device may comprise a rotatable driver shaft, a collar, and a guide. The collar may be coupled to the end of the rotatable driver. The guide may be sized and configured to mate with an implant. The guide may have an elongated neck including an engagement feature for coupling with a corresponding engagement feature of the collar. The implant holder and guide device may also comprise housing that receives the rotatable driver shaft at a distal end thereof. In accordance with some implementations, rotation of the housing may result in a corresponding rotation of the collar and coupling between the guide and collar engagement features.

This summary is provided to introduce a selection of concepts in a simplified form that are further described below in the detailed description. This summary is not intended to identify key features or essential features of the claimed subject matter, nor is it intended to be used to limit the scope of the claimed subject matter.

BRIEF DESCRIPTION OF THE DRAWINGS

The foregoing summary, as well as the following detailed description of illustrative embodiments, is better understood when read in conjunction with the appended drawings. For the purpose of illustrating the embodiments, there are shown in the drawings example constructions of the embodiments; however, the embodiments are not limited to the specific methods and instrumentalities disclosed. In the drawings:

FIG. 1 illustrates a side view of a driver device;

FIG. 2 illustrates a sectional view of the driver device of FIG. 1;

DETAILED DESCRIPTION

Figure 3:
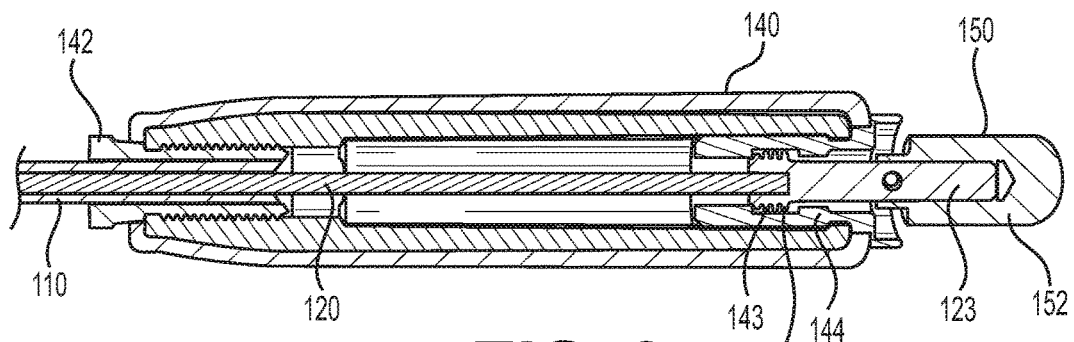
FIG. 3 illustrates a partial sectional view of the driver device of FIG. 1.

With references FIGS. 1-5, there is illustrated an articulating driver 100 used when fixing a spinal implant between adjacent vertebra. The articulating driver 100 can be used to prepare an opening/hole in the vertebral body for a bone screw, pin, anchor or other fastener. The articulating driver 100 can also be used to drive and/or locate the fastener in the vertebral body. For example, the driver 100 can be used as a jointed awl, a punch, a screw driver or a drill, or any other device known art used for preparing an opening and inserting a fastener into/proximate a vertebral body.

The driver 100 can include a rotatable driver shaft 110, a rod 120 disposed within the rotatable driver shaft 110, and a driver tip 130 for coupling to a screw/fixation element (or hole creating device such as a drill tip, punch, etc.) to the distal end of the rotatable driver shaft 110. The articulating driver 100 can also comprise housing 140 that receives the rotatable driver shaft 110 at a distal end thereof for facilitating rotation of the driver shaft 110/driver tip 130 to drive a bone screw. For example, the housing 140 can be coupled to the driver shaft 110 such that input torque received at the housing 140 is directly transferred to the driver shaft 110 and rotates, drives or otherwise actuates the driver tip 130, including any screw or drill component coupled to the driver tip 130. The housing 140 can also include a control element 150 disposed its proximal end. The control element 150 receives a proximal end of the rod 120 within the housing 140 for fixing the location of the rod 120 with respect to the housing and/or driver tip 130 components. The control element 150 can also be used to vary the amount of friction applied by the rod 120.

As shown in FIGS. 1 and 2, the driver 100 includes the rotatable driver shaft 110 capable of transmitting input torque to the driver tip 130. The input torque can be applied to the housing 140 or driver shaft 110 by hand or use of a power tool directly or indirectly coupled to the housing 140/driver shaft 110. The rotatable driver shaft 110, at its proximal end, can be connected to the housing 140. It is contemplated that the driver shaft 110 is fixedly coupled to the housing 140 such that rotation/movement of the housing 140 results in a corresponding rotation/movement of the driver shaft 110. The driver shaft 110 can be permanently and/or removably coupled to the housing 140, e.g., at an interior surface of the housing 140. The housing 140 can also include a mating sleeve 142, shown in FIG. 3, for coupling the driver shaft 110 to the housing 140. The driver shaft 110 can be permanently and/or removably coupled to the mating sleeve 142. The mating sleeve 142 can be permanently and/or removably coupled to the mating housing 140. For example, the mating sleeve 142 can be integrally formed with the housing 140 or a separate component from the housing 140. As illustrated in FIG. 3, the mating sleeve 142 can be coupled to the housing 140 via threads provided on an interior surface of the housing 140. As will be explained in further detail below, the control element 150 can also be coupled to the driver shaft 110 and/or the housing 140 directly or using a mating sleeve.

At its distal end, the rotatable driver shaft 110 forms driver tip 130. Components of the driver tip 130 can articulate with respect to the driver shaft 110 and/or rod 120 while transmitting input torque to a screw, fastener, drill, punch, etc. coupled to the driver tip 130. The driver tip 130 can be integrally formed with the driver shaft 110 or constructed as a separate component(s) coupled to the driver shaft 110. The driver tip 130 can include a ball-in-socket joint, a universal joint, or any other type of joint/connection known in the art that provides rotational and pivotal control between a drive shaft and drive interface.

Figure 4A:
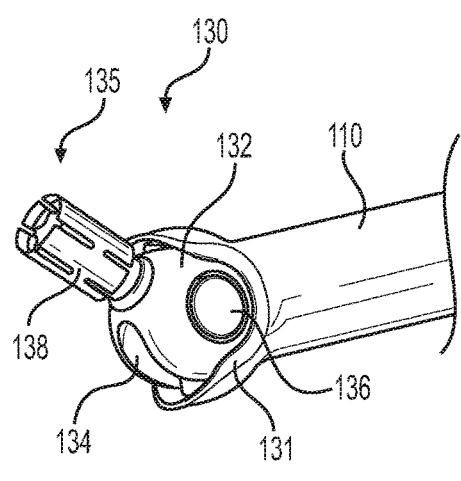
FIGS. 4A-4B illustrate a perspective views of the driver tip of FIG. 1.
Figure 4B:
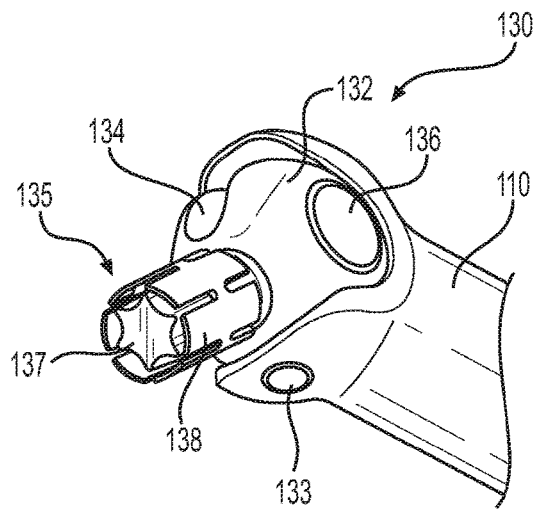
Figure 5:
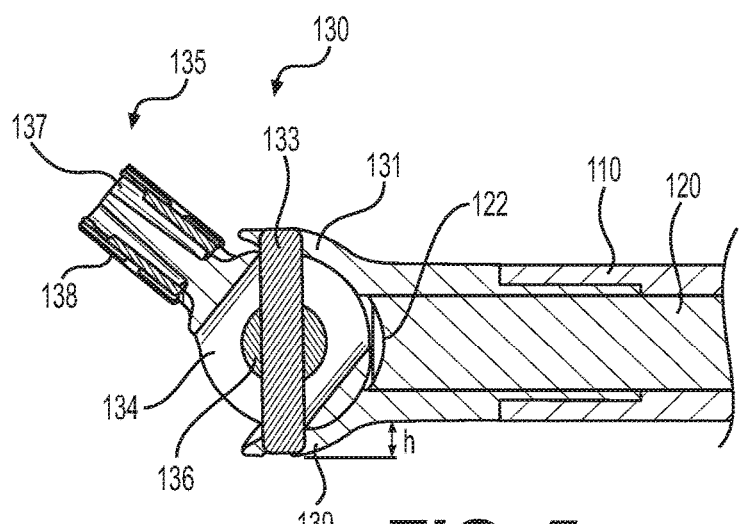
FIG. 5 illustrates a sectional view of the driver tip of FIGS. 4A and 4B.

As illustrated in FIGS. 4A, 4B and 5, the driver tip 130 can include a ball-in-socket joint. The driver tip 130 can include a domed/spherical-shaped mating surface 131 for mating with the spherical head 132 of the ball-in-socket joint. The spherical head 132 can form the proximal end of the driver tip 130. A pin 133 can extend through the spherical-shaped mating surface 131 and the spherical head 132, guiding the pivoting movement of the head 132 with respect to the mating surface 131. The pin 133 extends between opposite sides of the spherical mating surface 131 and through a slot 134 provided in the spherical head 132. The pin 133 ensures torque/rotational force applied to the driver shaft 110 is transmitted to an interface 135 provided for engaging a fixation or drill component. In particular, engagement and/or interference between the pin 133, spherical mating surface 131, and the head 132/slot 134 ensures that rotation of the driver tip 130/rotatable drive shaft 110 results in a corresponding rotation of the spherical head 132/interface 135. The pin 133 extends through a cross pin 136 provided in the spherical head 132. Rotation of the spherical head 132 on the cross pin 136 allows the spherical head 132 to pivot with respect to the mating surface 131 and/or rotatable drive shaft 110. It is contemplated that the pin 133 and cross pin 136 can be separately and/or integrally formed with respect to each other, the spherical head 132 and/or the mating surface 131 of the rotatable driver 110.

During operation, the user can rotate/pivot the head 132 with respect to the driver shaft 110/housing 140. Frictional engagement between the head 132 and the rod 120 fixes the location/rotation of the head 132 with respect to the driver shaft 110. Engagement between the head 132 and the rod 120 allows the user to select, and fix, the angle of the rod 120 with respect to the driver tip 130/interface 135. Thus, the driver tip 130 of the present disclosure can be positioned stably in a multi-angle screwing/unscrewing operation. For example, a ball-in-socket-type joint at the driver tip 130 can provide for approximately 35-55° of angulation, and the driver 100 can maintain the driver tip 130 within a useful range of operation. It is contemplated that the driver tip 130 can provide for a range of +/−45° of angulation of the interface 135 in comparison to the center axis of the rod 120. The angulation of the driver tip 130 can exist anywhere within a three dimensional plane based on the orientation of the spherical head 132 and mating surface 131, thereby allowing for rotation of the driver tip 130 in a multidirectional manner.

Referring to FIGS. 4A, 4B and 5, engagement of a screw or other fastener with the articulating driver 100/driver tip 130 will be described. It is contemplated that similar components and features could be utilized for coupling the driver shaft 110/driver tip 130 to a drill or other fixation tools. At its distal end, the driver tip 130 can include an interface 135 for engaging a screw/fixation element. The interface 135 can be, for example, threaded, keyed, or otherwise disposed to interact with a screw/fixation element. As provided in FIGS. 4A, 4B and 5, the interface 135 can include a drive element 137 that extends/projects from an outer surface of the driver tip 130. The drive element 137/interface 135 can have a size and shape that is complementary with a corresponding drive surface included on the head of a screw or other fixation device. When torque is applied by the driver tip 130, the drive element 137/interface 135 engages the head of the screw thereby to drive the screw/fixation element.

The interface 135 can comprise a self-retaining driver. For example, interface 135 can include a sleeve 138 extending over and/or around the drive element 137. As the drive element 137 engages the corresponding drive surface of a screw, arms of the sleeve 138 flex around and compress against the head of the screw. As a result, the screw is retained between the sleeve 138 and the drive element 137 when coupled with the interface 135. Once coupled, the user can rotate the driver shaft 110 in a manner which causes the interface 135 to interact with/drive the screw without worry that the screw will inadvertently disengage from the driver tip 130.

As illustrated in FIG. 2, the driver 100 includes a rod 120. The rod 120 extends from the housing 140, through a central channel provided the body portion of the rotatable driver shaft 110 to the driver tip 130. Illustrated in FIG. 5, the distal end of the rod 120 extends from the opening at the end of the channel. The end of the rod 120 can engage certain components of the driver tip 130 to limit and/or prevent rotation and pivoting movement of the driver tip 130/spherical head 132 with respect to the rod 120. For example, the end of the rod 120 can include a friction surface 122 sized and configured to engage the spherical head 132 of the driver tip 130. In another example, the rod 120 can include a mechanical engagement feature (e.g., key, recess, projection) that engages a corresponding feature on of the driver tip 130/ head 132. Engagement between these corresponding features limit and/or prevent rotation of the driver tip 130 with respect to the rod 120 and allow the user to select the desired angle between rod 120 and the driver tip 130.

In use, longitudinal/axial force can be applied to at proximal end of the rod 120 through engagement with the control element 150 (alternatively referred to herein as the frictional control element). In particular, the control element 150 may be used to operatively control the amount of friction/force with which the rod 120 engages the spherical head 132 of the driver tip 130. The friction/force applied to the spherical head 132 can vary, or can be constant based on manipulation and design of the control element 150. For example, the amount of friction/force exerted through the control element 150 can be a constant state of friction/force. Alternatively, the rod 120 can engage the spherical head 132 with variable friction/force. For example, the amount of friction/force exerted upon the spherical head 132 by the rod 120 can vary according to the amount of friction/force with which the user engages the control element 150.

Alternatively, various "set" positions can exist within the control element 150, such that a user can select a predetermined amount of friction. In one example, the control element 150 can be "locked" into place via engagement with the housing 140, such that the amount of friction with which the control element 150 engages the rod 120 and the amount of friction with which the rod 120 engages the driver tip 130/spherical head 132, is constant when the control element 150 is in the locked position. As illustrated in FIG. 3, the distal end of the control element 150 can include an engagement feature 151 (e.g., threads, projections, teeth, barbs) sized and configured to engage a corresponding feature 143 provided on an interior surface of the housing 140. As the engagement feature 151 (e.g., threads) of the control element 150 engage the engagement feature 143 (e.g., threads) of the housing 140, the rod 120 moves laterally within the driver shaft 110 causing the distal end/friction surface 122 to engage/disengage the driver tip 130/spherical head 132.

As described above, the control element 150 can be translated axially, towards/away from the distal end of the driver 100 to increase/reduce the amount of pressure applied by the rod 120 to the driver tip 130/head 132. When the engagement features 151/143 are engaged, pressure applied by the rod 120 on the head 132 remains constant and the control element 150 is considered in a "locked" position. For example, when the engagement feature 151 and corresponding features 143 of the housing 140 comprise threads, as rotational force is applied to the control element 150 the control element 150 and rod 120 traverse the housing 140 causing a lateral force to be applied to the driver tip 130/head 132.

In another example, the control element 150 can include a spring or other feature engaged between the control element 150 and the rod 120 that provides variable pressure/ force to the rod 120. The user can manipulate the control element 150 via axial movement, rotation, pushbutton, etc. to adjust the pressure/force applied to the rod 120.

As illustrated in FIG. 3, the control element 150 can include a knob 152. The knob 152 can function as a dial, pushbutton, or other means to enable the user to control force/pressure on the rod 120. The knob 152 can be removably or permanently coupled to the control element 150. Likewise, the knob 152 can be removably or permanently coupled to the rod 120. As provided in FIG. 3, the knob 152 can be coupled to a rod engagement sleeve 123 that is fixedly or removably coupled to the rod 120. The engagement features 151 for engaging the housing 140 can be provided on the sleeve 123.

In another example, the engagement features 143 can be provided on a sleeve 144 that is, in turn, fixed to/with respect to the housing 140. The sleeve 144 can extend within the housing 140 at a fixed position such that the knob 152/ engagement features 151/rod engagement sleeve 123 move laterally with respect to both the sleeve 144 and the housing 140.

In some implementations, the various components of the driver 100 may have the following dimensions. The radius of curvature of the spherical mating surface 131 may be approximately 3.6 mm and may have a depth of 1.8 mm. The spherical head 132 portion may have a diameter approximately 6.5 mm. The retention cap portion 139 of the driver tip 130 may have a total height (h) of 3.0 mm (i.e., height difference between the outer radius/surface of the driver shaft 110 and the outermost radius/surface of the retention cap portion 139). The driver tip 130 may have a length of 15 mm. The interface 135 may have a depth of 3.5 mm.

Referring now to FIGS. 6-9, illustrated herein is an example implant holder and guide device 200 with a detachable guide 230. A vertebral spacer 205, bone graft, or other interbody fusion device can be coupled to the implant 232/guide 230 for insertion between adjacent vertebral bodies. Openings included in the guide 230 provide access for bone screw placement and insertion. To improve visibly and access to the surgical site, various components of the guide device 200 can be removed. For example, the guide 230 can be detached from the implant 232 before the user fixes the implant/spacer in place via insertion of a bone screw into the implant 232, spacer 205, and associated vertebral body. The shaft 210 of the holder and guide device 200 can also be detached from the guide 230, with the guide 230 remaining coupled to the implant 232, before insertion of the bone screw into the associated vertebral body. In another example, the shaft 210 and the collar 233 can be removed. Finally, the housing 240 can be removed from the shaft 210, leaving the shaft 210, collar 233 and guide 230 in place during the fixation procedure.

Figure 6:
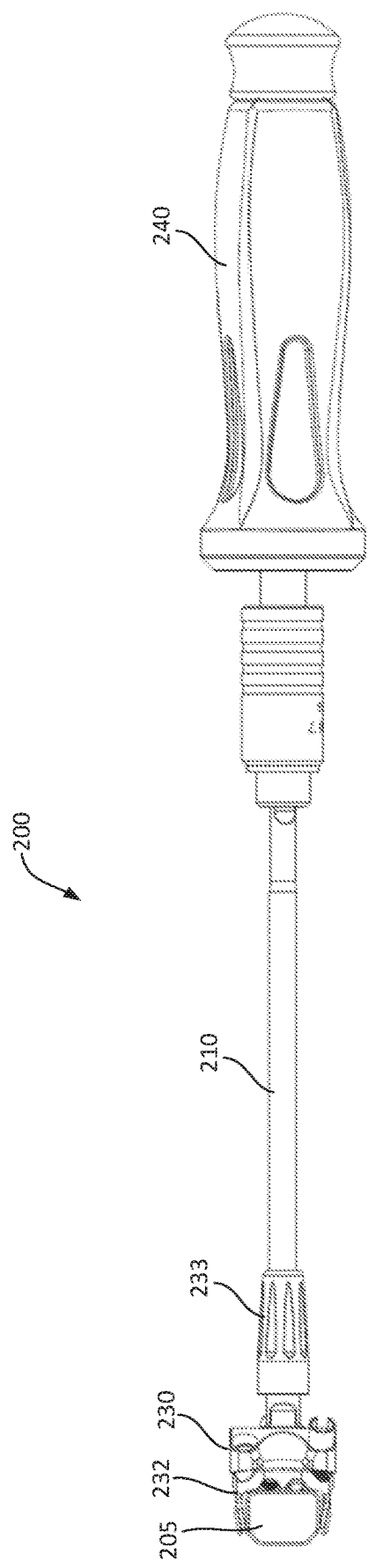
FIGS. 6-9 illustrate top, side, and opposing end views of an implant holder and guide device.
Figure 7:
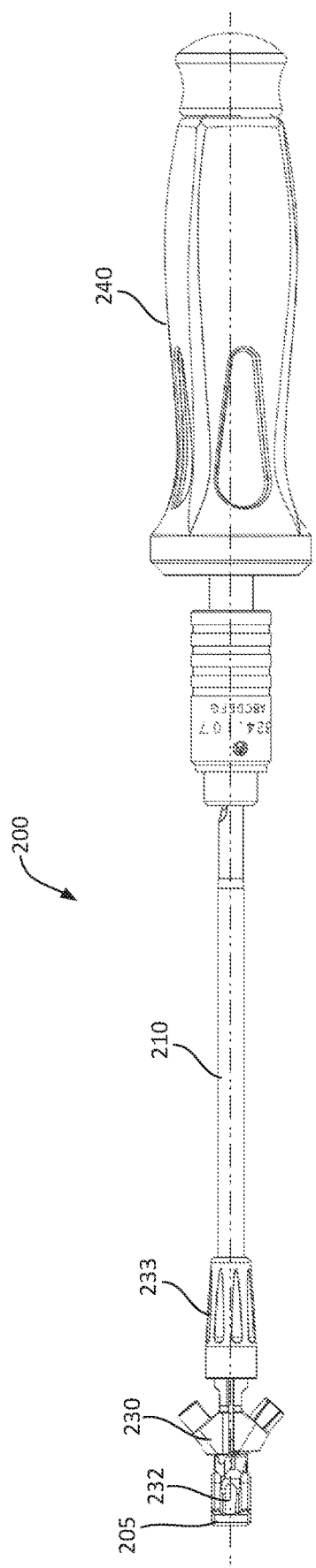
Figure 9:
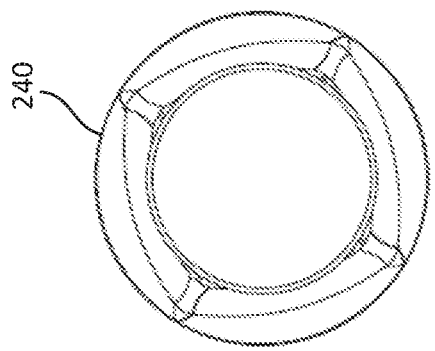
Figure 8:
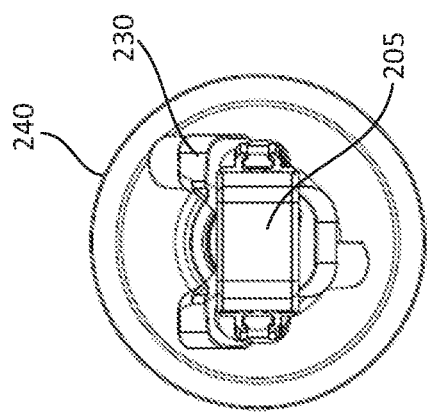

FIG. 6 provides a top view and FIG. 7 provides a side view of the implant holder and guide device 200 with a detachable guide 230, implant 232 and spacer 205 attached. FIGS. 8 and 9 provide opposite end views of the implant holder and guide device 200. As illustrated in FIGS. 6 and 7, the detachable guide 230 can be disposed at the distal end of the implant holder and guide device 200. The detachable guide 230 includes an inner guide body 231 and an implant 232 (illustrated in FIG. 14). A spacer 205, bone graft, or other interbody fusion device can be coupled to the distal end of the guide 230, at the implant 232, for insertion and placement in the vertebral disc space. A collar 233 engages the distal end of the rotatable driver shaft 210 and provides a coupling between the driver shaft 210 and the main guide body 231.

Figure 10:
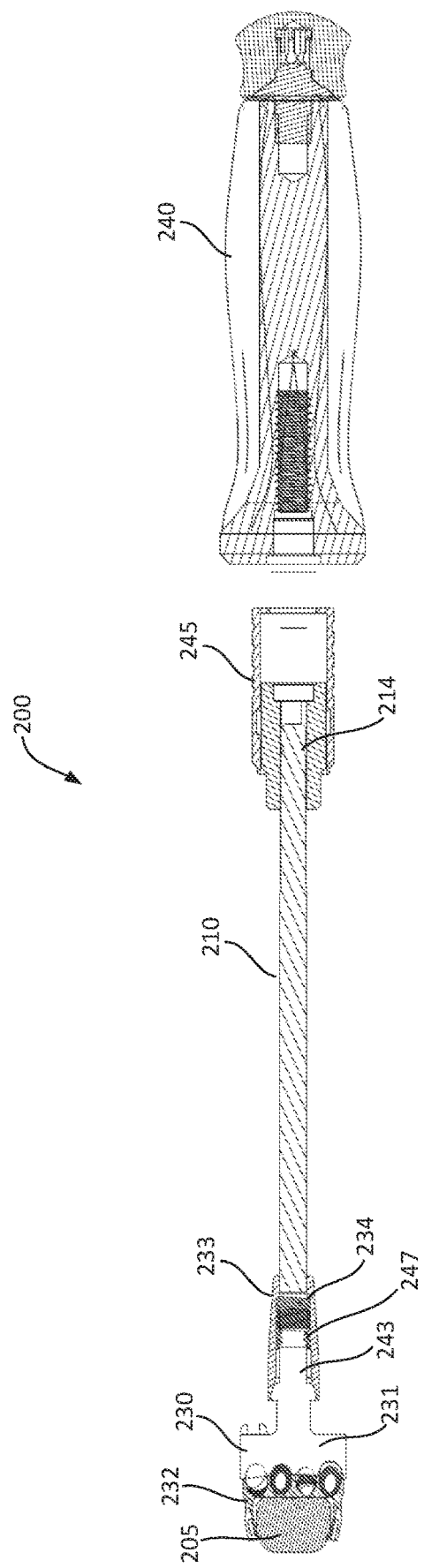
FIG. 10 illustrates a top sectional view of the implant holder and guide device of FIG. 6.

Similar to the housing 140 described above with respect to the driver 100 (illustrated in FIG. 3), FIGS. 6, 7, and 10 provide a housing 240 for use with the implant holder and guide device 200. By manipulating the location of the housing 240, the user is able to locate/plate the guide 230, implant 232 and spacer 205 within the patient. The driver shaft 210 can be fixedly coupled to the housing 240 such that rotation, tension, compression, or any other movement of the housing 240 results in a corresponding movement of the driver shaft 210/guide 230. The guide device 200 can include a coupling 245, e.g., quick connect coupling, for joining the driver shaft 210 to the housing 240. The coupling 245 can include an opening to receive a proximal end of the driver shaft 210. Rotational and axial movement of the driver shaft 210 can be fixed with respect to the housing 240 at the coupling 245. As described with respect to FIG. 22, coupling 245 can include one or more engagement features for engaging corresponding key feature or recess 214 of the driver shaft 210 to fix the rotational and/or axial movement of the driver shaft 210. The coupling 245 can be fixedly or removably coupled to the housing 240. For example, as illustrated in FIG. 10, the coupling 245 can be threaded into the housing 240.

FIG. 10 provides a cross-sectional view of the guide 230. The driver shaft 210 interacts with the detachable guide 230 at the distal end of the implant holder and guide device 200. For example, the driver shaft 210 can be permanently or removably coupled to the collar 233 which is, in turn, coupled to the guide body 231. As illustrated in FIG. 10, the driver shaft 210 can threadably engage a threaded interface 234 provided on the collar 233. The driver shaft 210 can be detached from the guide 230 during the implantation procedure to allow for increased visibility and access.

Figure 18:
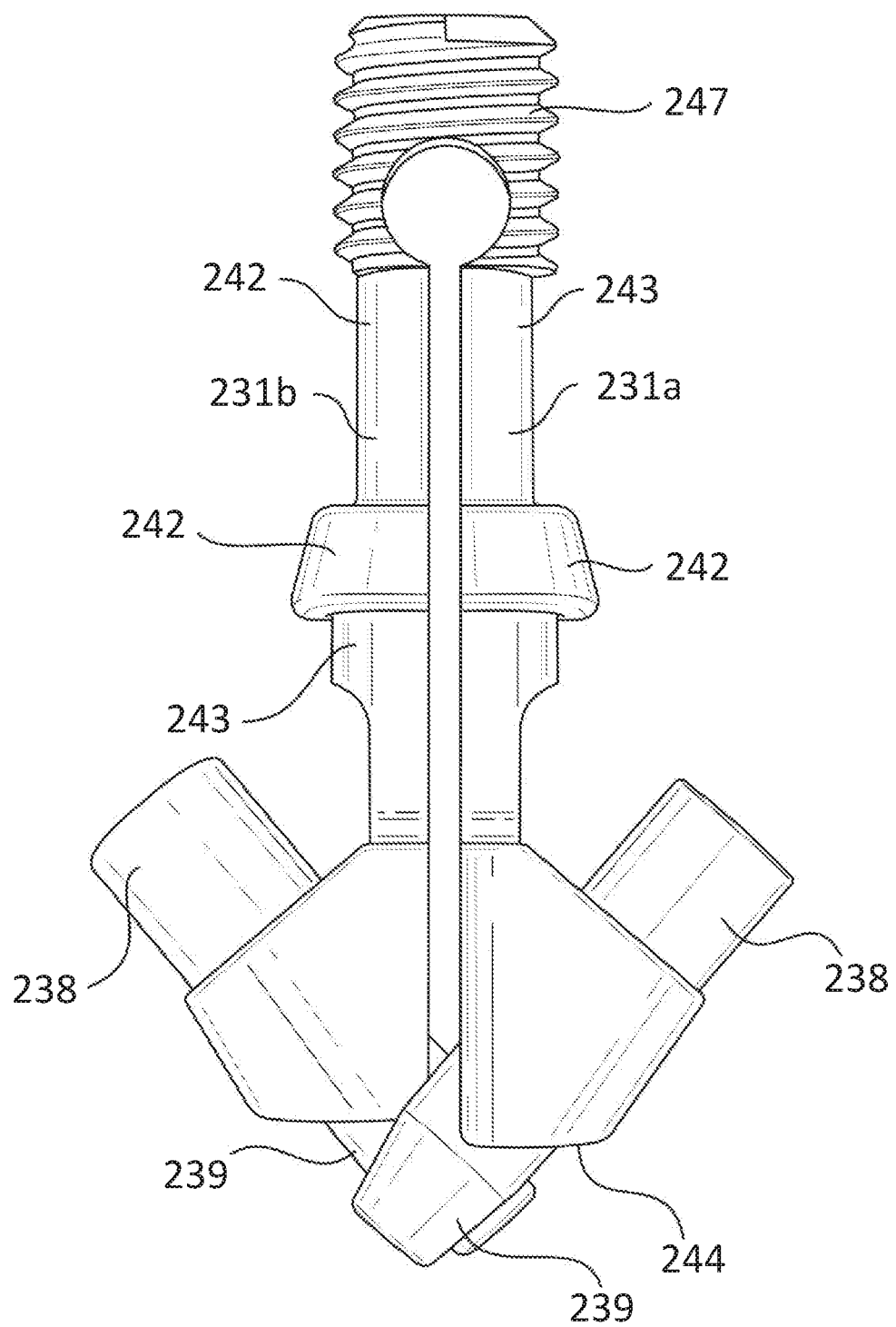
FIG. 18 illustrates a side view of the guide of FIG. 16.

The guide 230/guide body 231 can be threadably coupled to the collar 233. For example, the guide body 231 can include a threaded interface 247 provided on the neck 243 of the guide body 231 for engaging the threaded interface 234 provided on the collar 233. The guide body 231 can be formed to include spaced apart opposing halves (231a, 231b) joined together at their proximal end (see e.g., FIG. 18). During operation, as the driver shaft 210 is rotated (via rotation of housing 240) torque is transmitted to the collar 233 causing the collar 233 to engage the guide 230. As the collar 233 is translated towards the distal end of the holder and guide device 200 (e.g., by rotation of the collar 233 and engagement with the guide body 231), opposing halves (231a, 231b) of the guide body 231 move together. In moving opposing halves of the guide body 231 together/towards each other, the guide body 231 compresses against the associated implant 232 and secures the implant 232 to the guide 230. Likewise, the guide 230 can be removed from the implant 232 by disengagement between the collar 233 and the inner guide body 231 and the corresponding movement/separation of the guide body halves (231a, 231b).

Figure 11:
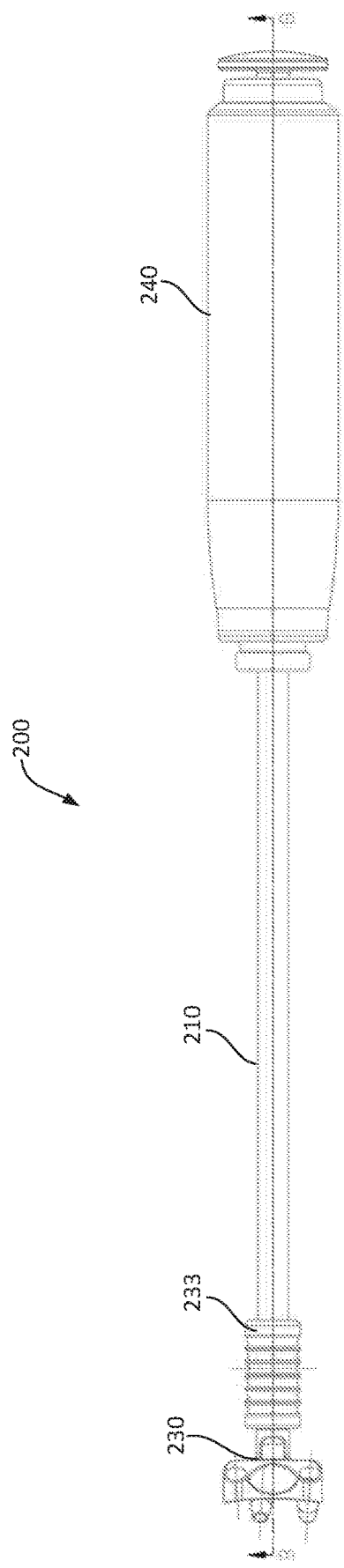
FIG. 11 illustrates a top view of an implant holder and guide device.
Figure 12:
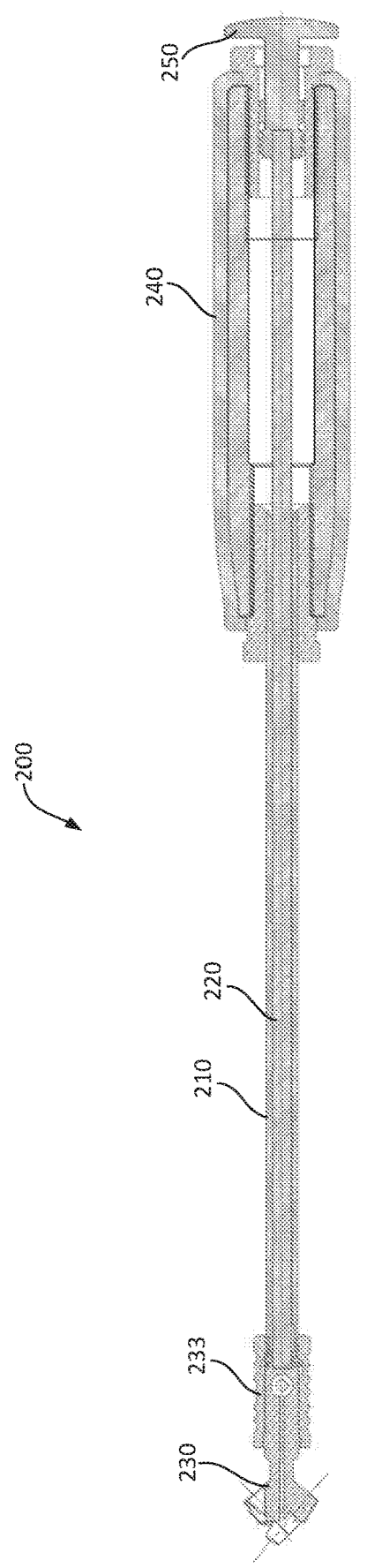
FIG. 12 illustrates a side sectional view of the implant holder and guide device of FIG. 11.

FIG. 11 provides a top view of an example implant holder and guide device 200 and detachable guide 230 without either an implant or spacer attached. FIG. 12 provides a side cross-section view of the implant holder and guide device 200 of FIG. 11. The implant holder and guide device 200 can include a housing and shaft structure similar to the driver 100 described above. For example, the implant holder and guide device 200 can include a rotatable driver shaft 210, a rod 220 disposed within the rotatable driver shaft 210, housing 240 that receives the driver shaft 210, and a control element 250.

Figure 13:
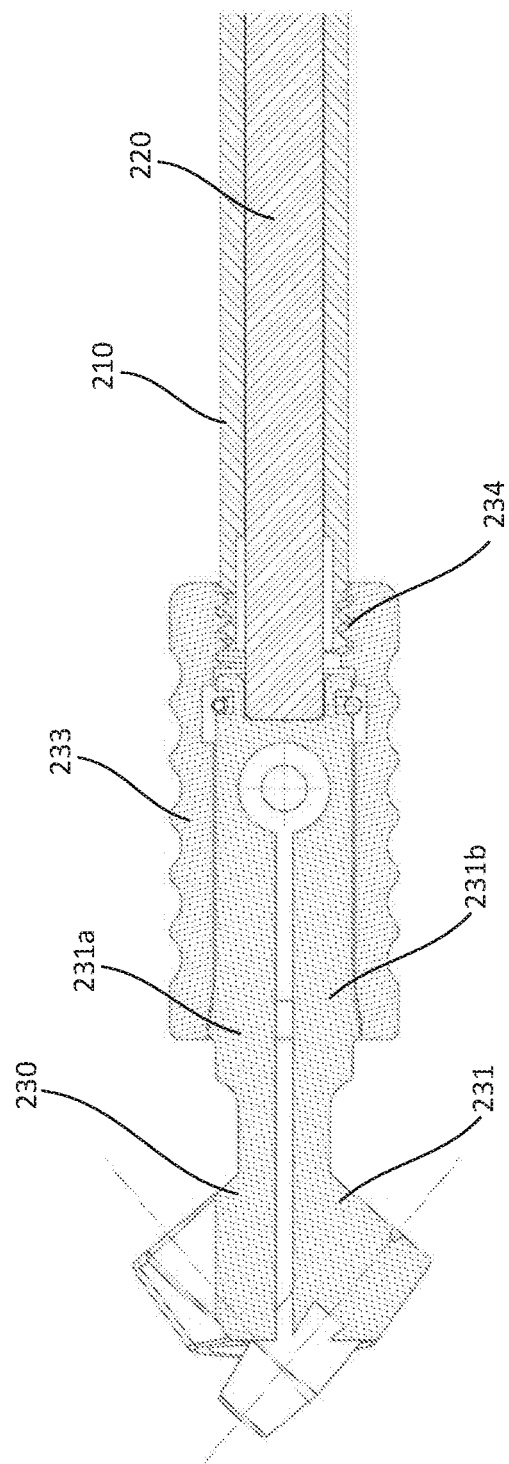
FIG. 13 illustrates a partial side sectional view of the implant holder and guide device of FIG. 11.

As illustrated in FIG. 13, the driver shaft 210 can be threadably coupled to the collar 233 at a threaded interface 234 provided on the collar 233. The rod 220 extends within the driver shaft 210 and can be received within a recess provided in the proximal end of the guide 230. The driver shaft 210 and rod 220 can be detached from the guide 230 during the implantation procedure to allow for increased visibility and access.

The guide 230/guide body 231 can also be threadably or otherwise coupled to the collar 233. The guide body 231 can include spaced apart opposing halves (231a, 231b) joined together at their proximal end. As the driver shaft 210 is rotated (via rotation of housing 240) torque is transmitted to the collar 233 causing the collar 233 to engage the guide 230. As the collar 233 is rotated and translated towards the distal end of the holder and guide device 200, an angled cam surface of the collar 233 engages a corresponding angled cam surface of the opposing guide body halves 231a, 231b. As a result, the opposing halves 231a, 231b of the guide body 231 move together and the guide body 231 compresses against the associated implant 232.

Figures 14, 15:
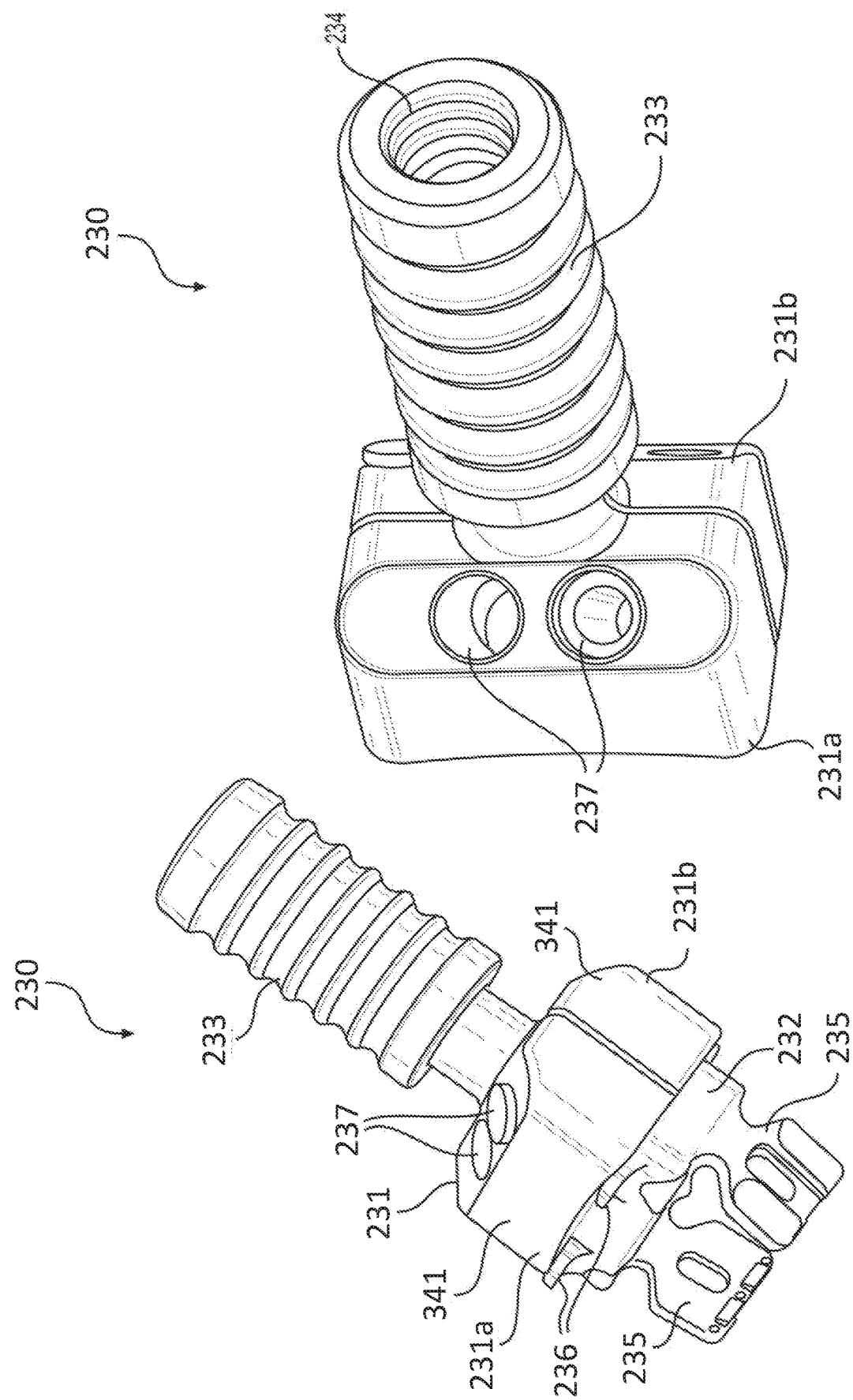
FIGS. 14 and 15 illustrate perspective views of a guide and implant.

Referring FIGS. 14 and 15, the detachable guide 230 can include an implant 232. The implant 232 can be removably or permanently coupled to a spacer 205, bone graft, or other interbody fusion device. To increase stability of the spacer, the implant 232 remains coupled to the spacer following insertion and removal of the guide body 231 from the patient. That is, the implant 232 can remain coupled to the spacer/bone graft and permanently remain in the patient as part of the implant.

The implant 232 can include arms 235 extending from the distal end and/or sides of the implant 232. The arms 235 can be expanded/flexed in a direction away from the centerline of the holder and guide device 200 and around a spacer. Pressure applied by the arms 235 secure the spacer to the implant 232. The arms 235 can include engagement features (e.g., projecting teeth) that engage the implant. The implant 232 can include stops 236 extending from a side surface of the implant 232 to control insertion of the spacer/implant 232 into the vertebral disc space. Stops 236 can be sized and configured to interfere/contact various anatomical structure to control the depth and location of spacer/implant 232 placement. For example, stops 236 can be used to prevent insertion of the inner guide body 231 into the disc space. The coupling between the spacer, implant 232 and inner guide body 231 secure the guide 230 in place when it is detached from shaft portions of the implant holder and guide device 200.

As illustrated in FIGS. 14 and 15, the inner guide body 231 can include a number of openings 237. The openings 237 provide access for and guide bone screw placement and insertion into the implant 232/spacer/vertebral body. An operator may couple the spacer to the vertebral body by inserting the screw into an appropriate one of the openings 237. The screw will pass through the opening 237 and out of the guide 230. The screw may engage the implant 232 and secure the implant 232 in the patient and permanently couple the implant 232 to the spacer.

Figure 16:
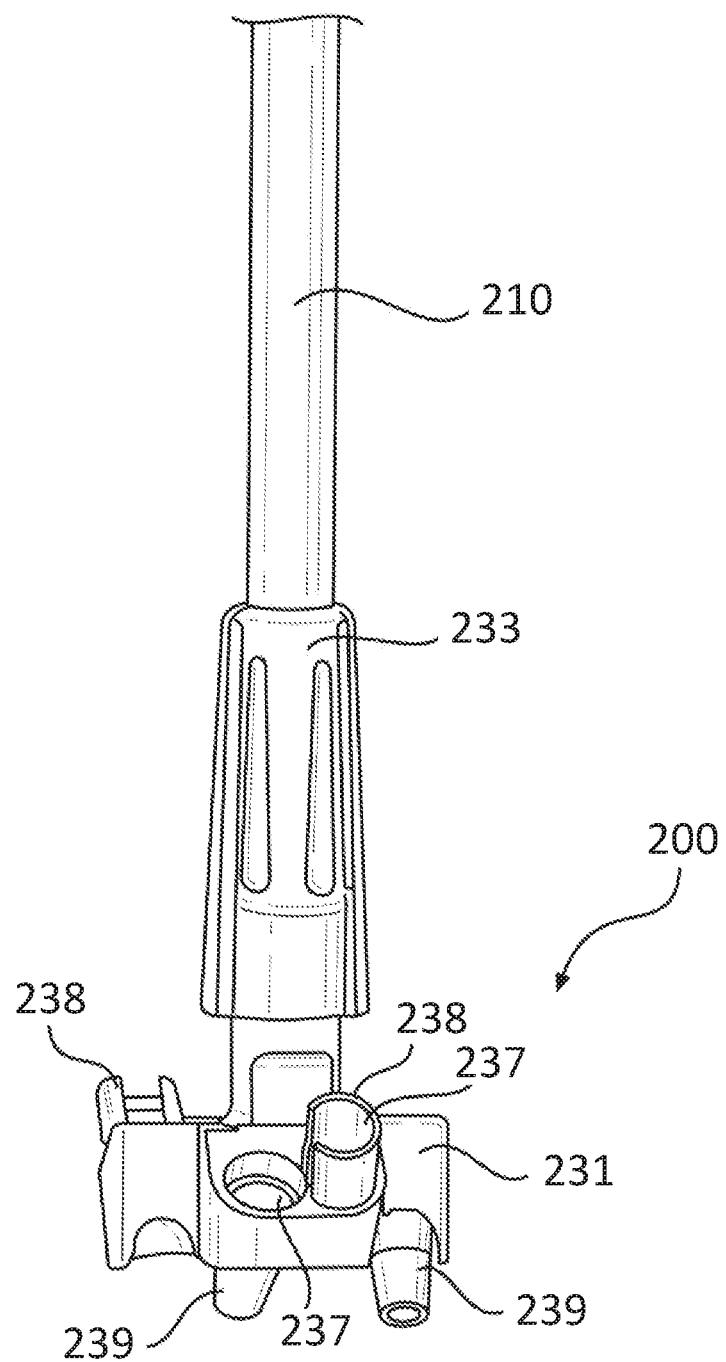
FIG. 16 illustrates a partial perspective view of the implant holder and guide device of FIG. 6.

In some examples, as illustrated in FIGS. 14 and 16, the implant holder and guide device 200 can include blocks 341 extending over the guide body 231. Opposing blocks 341 can be provided to fit over the opposing halves 231a, 231b of the guide body 231. The blocks 341 can extend between the shoulder 242 (see FIG. 18) extending from the neck 243 of the opposing halves 231a, 231b to the bottom surface 244 of the guide body 231. All or a portion of the shoulder 242 may be received within the blocks 341.

Figure 17:
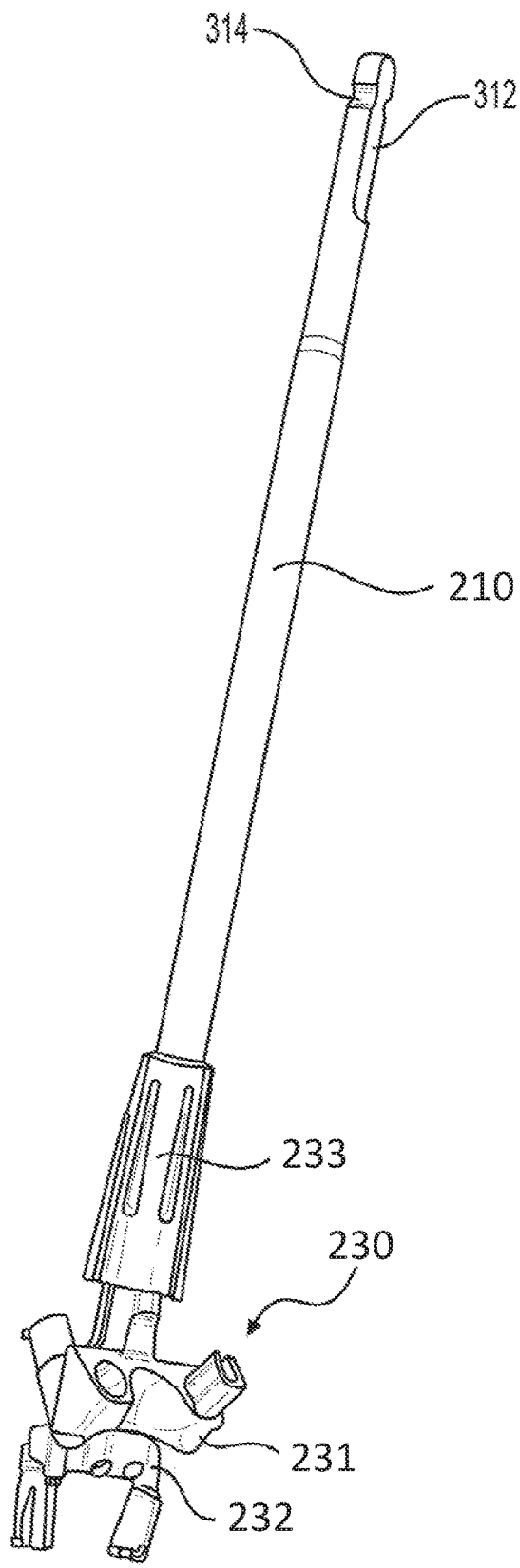
FIG. 17 illustrates a perspective view of the implant holder and guide device of FIG. 6.
Figure 19:
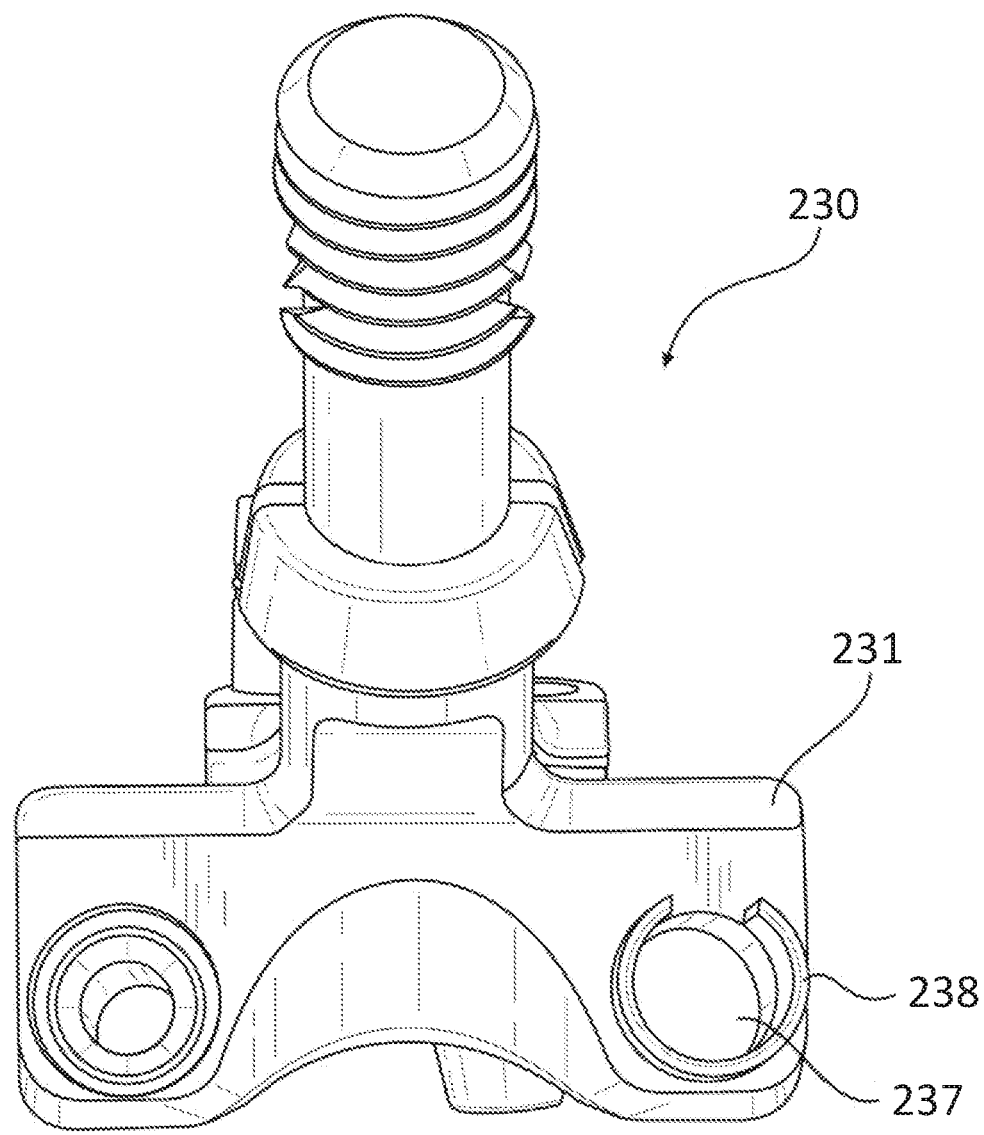
FIG. 19 illustrates a top perspective view of the guide of FIG. 16.
Figure 20:
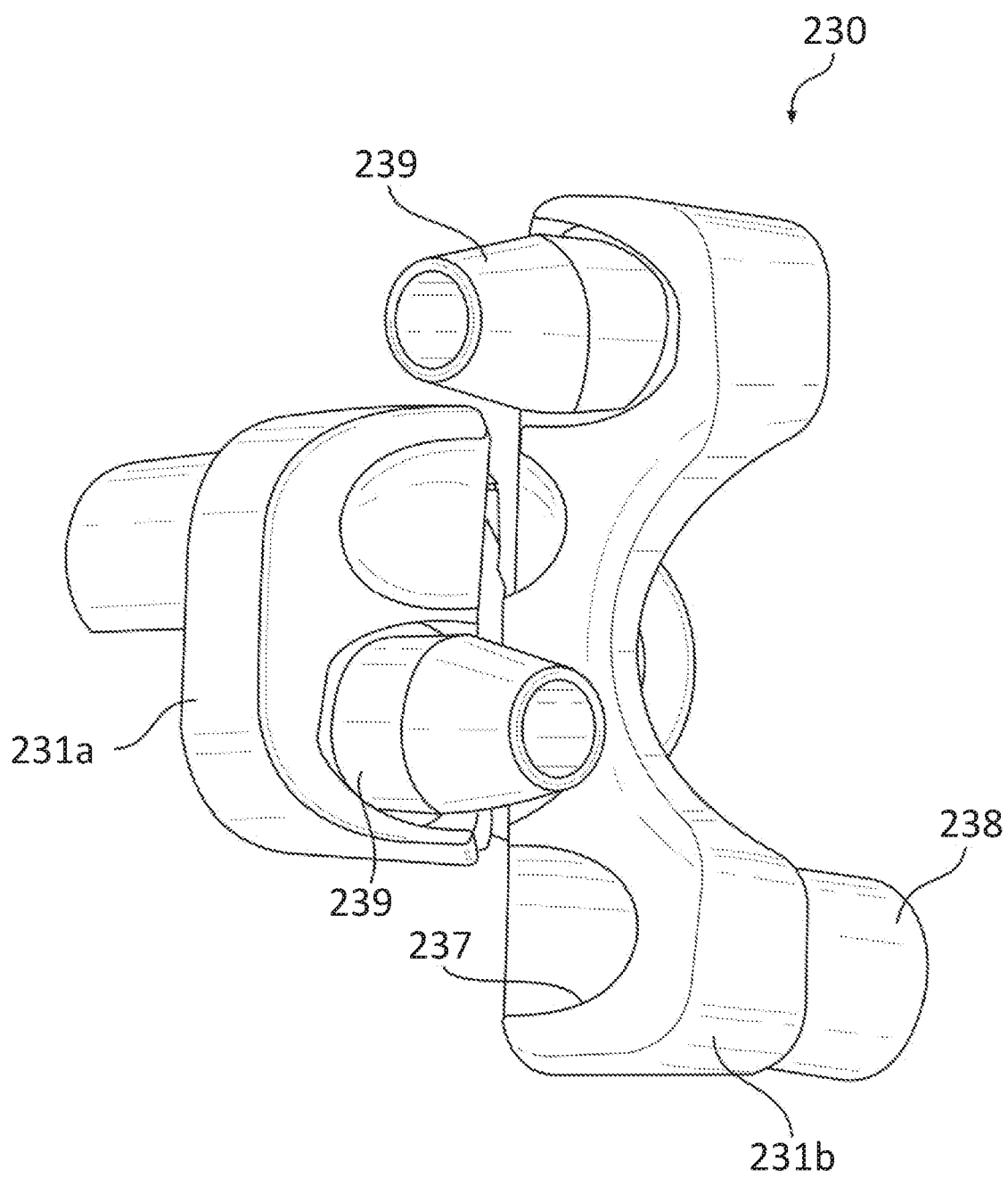
FIG. 20 illustrates a bottom view of the guide of FIG. 16.

FIGS. 16 and 17 provide perspective views of the distal end of the example implant holder and guide device 200 of FIG. 6. As illustrated in FIG. 16, the guide body 231 can include sleeves 238 projecting from around the openings 237. These sleeves 238 provide guidance and support for a screw or other instrument inserted into the opening 237. Likewise, projections 239 extending from the bottom surface of the guide body 231 are sized and configured to engage a corresponding opening in the implant 232. As illustrated in the guide 230 depicted in FIGS. 18-20, the projections 239 can include a conical-shaped end to facilitate advancement into openings provided in the implant 232. The projections 239 can extend at an angle from the bottom surface 244 of the guide 230 such that as the opposing halves 231a, 231b of the guide body 231 are brought together, an implant 232 coupled to the guide 230 at projections 239 is drawn up the projections 239 toward/in contact with the bottom surface 244 of the guide 230. The projections 239 can also include a central opening extending therethrough. The central opening can provide access for awl, punch, drill, driver, or any other device known art used for preparing an opening and/or guiding and inserting a fastener through the guide 230 and into/proximate a vertebral body.

Figure 21:
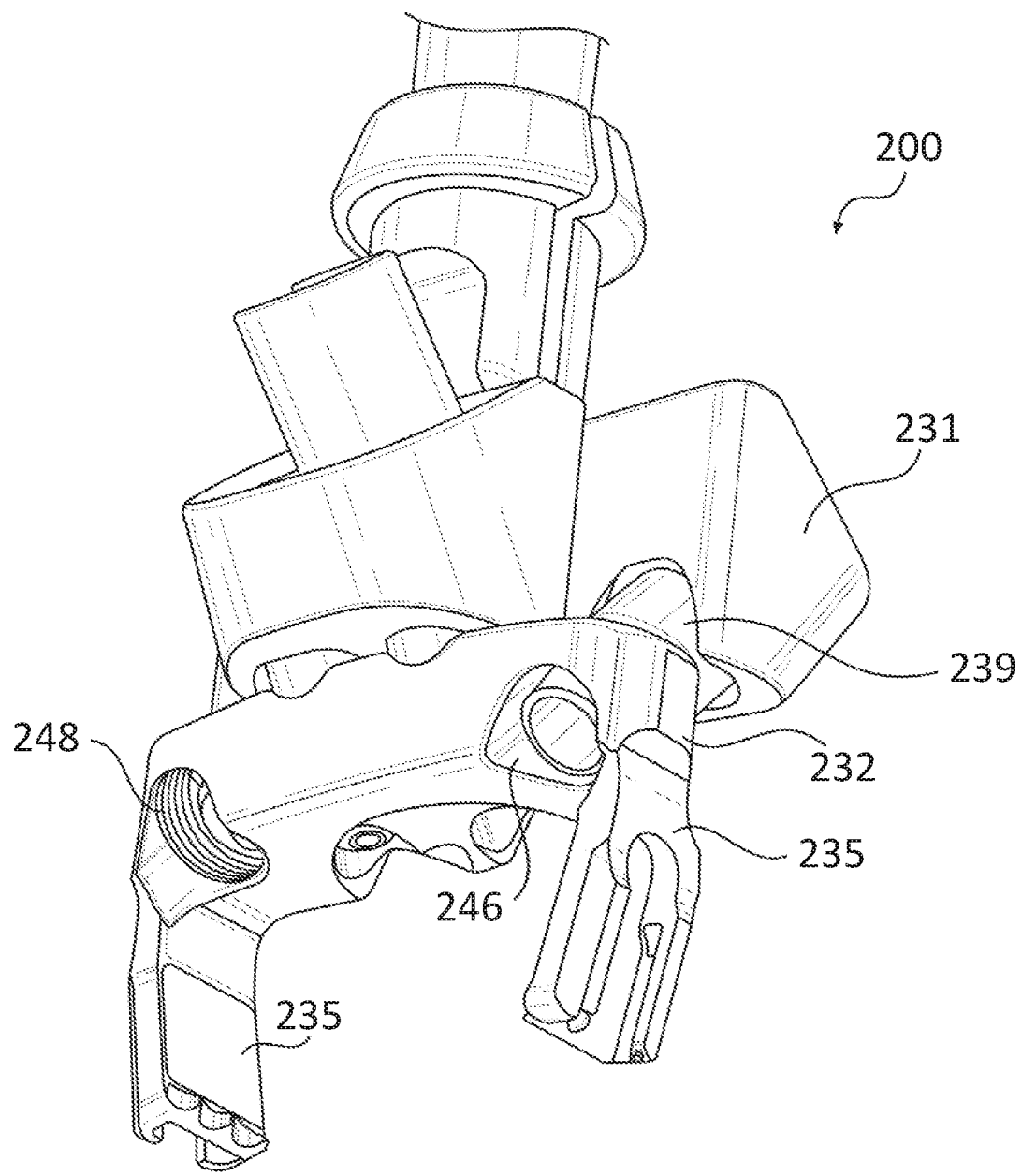
FIG. 21 illustrates a bottom perspective view of the guide and implant of FIG. 16.

FIG. 21 illustrates a bottom perspective view of the implant holder and guide device of FIG. 16 with an implant 232 attached. As described above, the projections 239 extend from the bottom surface 244 of the guide body 231 are sized and configured to engage a corresponding opening 246 in the implant 232. Likewise, as the implant 232 is intended to remain in the patient and permanently coupled to the spacer, the bone screw may engage threads 248 (or other fastener feature) provided in the corresponding opening 246 of the implant 232. The implant 232 includes arms 235 for coupling to an implant. The arms 235 can include projects/recesses for engaging and retaining the implant on the implant 232. Likewise, the arms 235 can include one or more grooves on the outer surface of the arm 235 for engaging the spacer.

Figure 22:
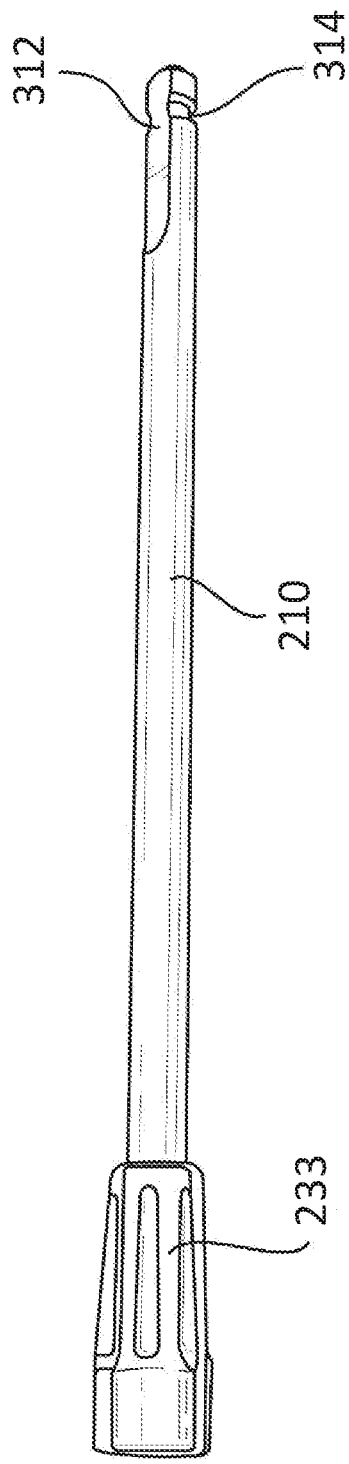
FIG. 22 illustrates a perspective side view of a rod and collar.

FIG. 22 illustrates a perspective side view of a driver shaft 210 and collar 233. The collar 233 may be fixedly or removably coupled to the driver shaft 210. Likewise, the collar 233 may have a fixed position with respect to the driver shaft 210 or the collar 233 may be move (rotate, translate longitudinally) with respect to the driver shaft 210. As illustrated in FIG. 22, the proximal end of the driver shaft 210 can include a key feature 312 sized and configured to couple with the corresponding housing and/or control element. The key 312 can ensure rotational movement of the driver shaft 210 corresponds to similar movement of the housing/control element. Likewise, the proximal end of the driver shaft 210 can include a recess 314 sized and configured to engage a corresponding engagement feature of the housing. Coupling between the recess 314 and the housing can be used to fix longitudinal/axial movement of the driver shaft 210 with respect to the housing.

Figure 23:
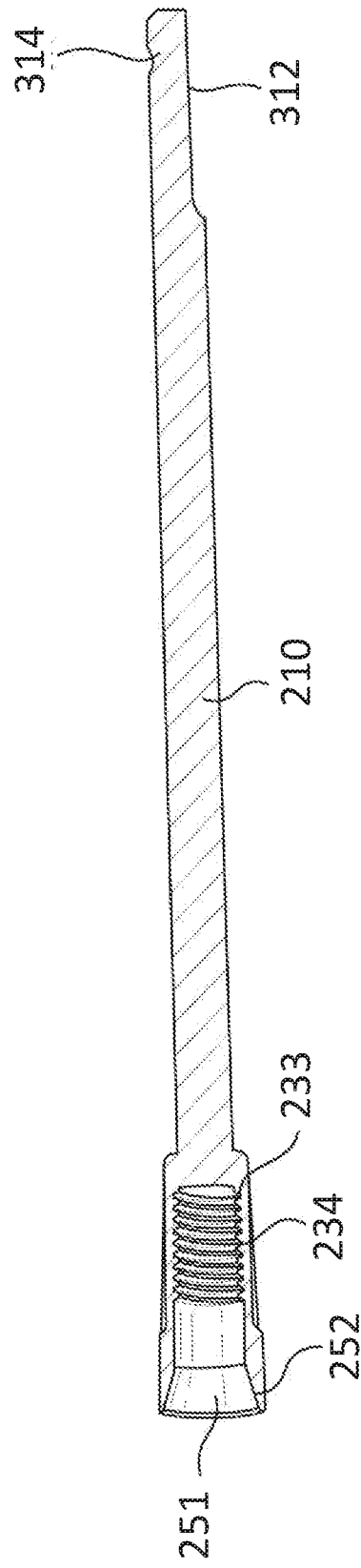
FIG. 23 illustrates a sectional view of the rod and collar of FIG. 22.
Figure 24:
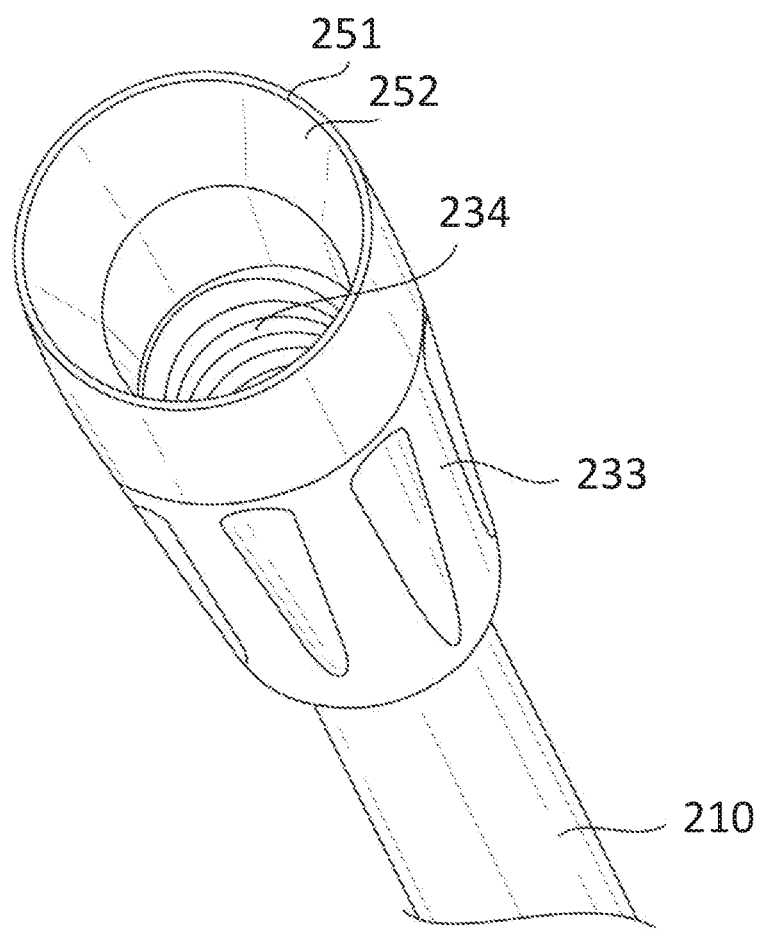
FIG. 24 illustrates a perspective end view of the collar of FIG. 22.

FIG. 24 provides a perspective view of the distal end of the collar 233 and driver shaft 210. As described above, the collar 233 can include a threaded interface 234 for engaging the rod and/or guide. For example, the threaded interface 234 can engage a corresponding threaded interface 247 provided on the guide 230. As illustrated in FIG. 23, the driver shaft 210 and collar 233 can have unitary construction. Accordingly, rotational movement of the driver shaft 210 results in corresponding rotational movement of the collar 233. As a result, the collar 233 can engage/disengage the guide 230 and can draw the opposing halves 231a, 231b of the guide body 231 together/apart. The threaded interface 234 can be recessed within the collar 233. The opening 251 at the distal end of the collar 233 can be sized to accommodate the neck 243 of the guide body 231, including all or a portion of the shoulder 242. The opening 251 can also be sized such that all, or a portion of, the shoulder 242 is prevented from extending within the opening. For example, as illustrated in FIGS. 10 and 12, the opening 251 can include a cam/tapered surface 252 corresponding to a taper of the shoulder 242 or other portion of the guide body 231. Interaction/contact between the tapered surface 252 and the shoulder 242 can cause the opposing halves 231a, 231b of the guide body 231 to draw together/move apart.

As described above, the driver 100 and implant holder/guide device 200, 300 include housings 140, 240 at their proximal end. The housings 140, 240 can include a control element 150 for controlling driver tip 130/guide 230 functionality. While the control element 150 has been depicted as extending from the proximal end of the housing 140, 240 it is contemplated that the control element 150, may have different shape, location and interaction with the housing 140, 240. For example, the control element 150 may be disposed laterally along housing 140, 240, or at the distal end of housing 140, 240. Actuation of the control element 150 can engage the proximal end of the rod 120, 220, moving the driver tip 130/inner guide body 231 laterally with respect to the shaft 110, 210.

Figure 25:
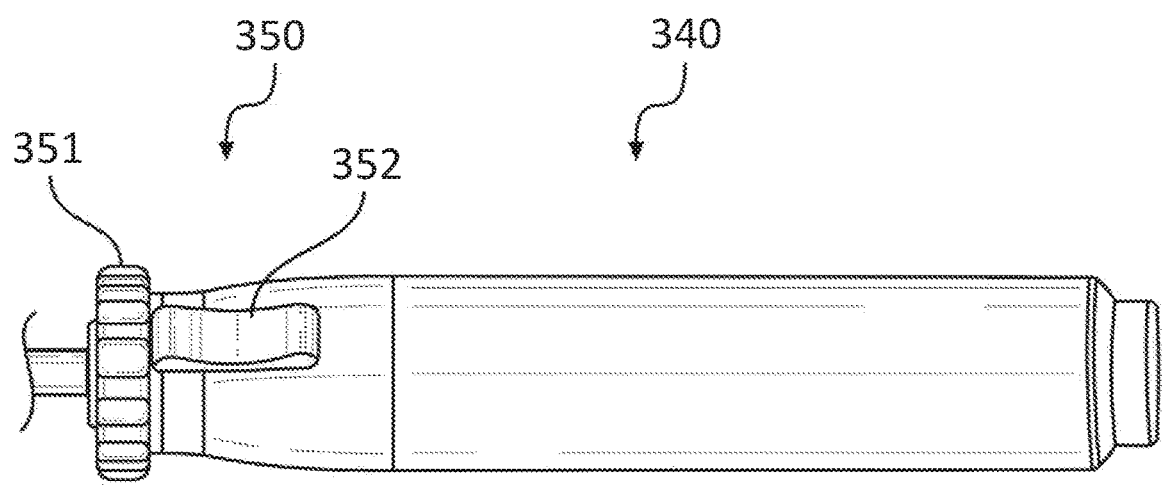
FIGS. 25-27 illustrate a side views of example housings.
Figure 26:
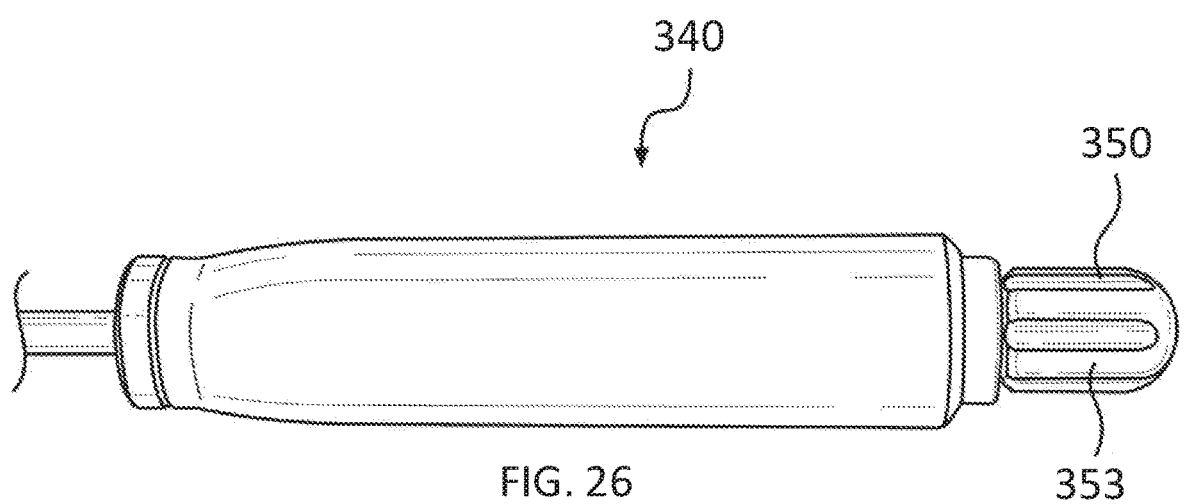
Figure 27:
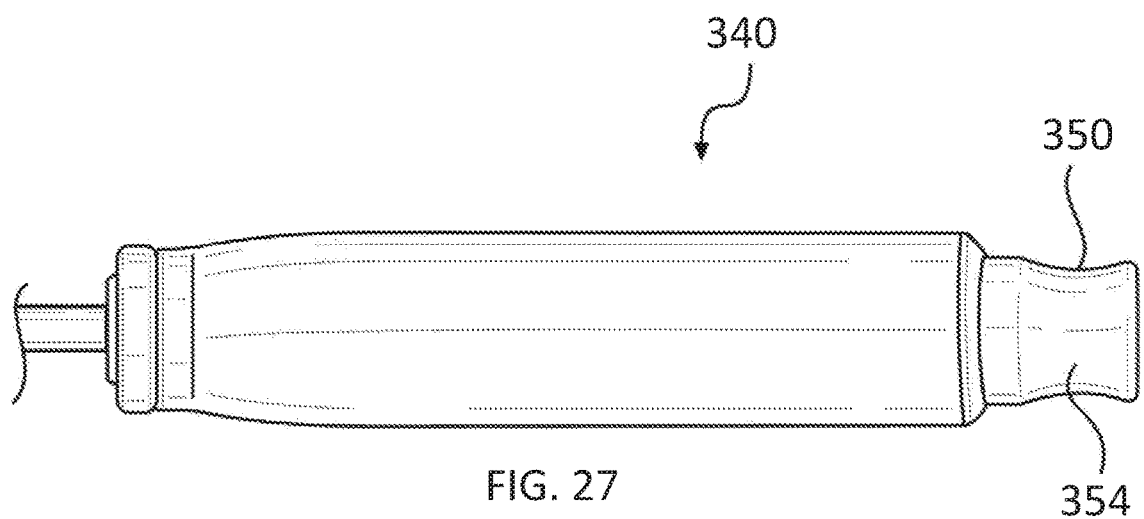

Various examples of control elements and their relationship to the housing are shown in FIGS. 25-27. FIGS. 25-27 provide a housing 340 similar in size and function to the housings 140, 240. The housing 340 can be coupled to the proximal end of the driver and the implant holder and guide device in any of the disclosed examples.

FIG. 25 shows an example housing 340 having a control element 350 including a dial 351 and a lever lock 352 mechanism. In an example housing 340, the dial 351 can be rotatably disposed along the distal end of the housing 340 and the lever lock 352 can be provided proximal the dial 351. The dial 351 and lever lock 352 allow the user to set the desired angle of the driver tip/implant holder/guide device. For example, the user can move the housing 340 to the desired angle (manually) and set the desired tension/drag between the driver tip/guide and the driver shaft/rod using dial 351. The dial 351 can also be used to lock the angle of the driver tip/implant holder/guide device with respect to the driver shaft/rod. The housing 340 can include a lever lock 352 used to release the housing 340 from the driver or implant holder/guide device 200 (e.g., release the housing from the driver shaft/rod).

FIG. 26 shows an optional housing 340 having a control element 350 that includes a rotatable knob 353. The desired angle of the device can be set by manually moving the housing 340 with respect to the driver tip/guide. The angle is held using the control element 350 mechanism and controlled by rotation of the knob 353. For example, tension between the rod and the driver tip/guide is controlled by rotation of the knob 353 and can be released by rotation of the knob 353 in the opposite direction. Optionally, the amount of tension can be set/fixed by a locking mechanism used in conjunction with the knob 353.

FIG. 27 shows an optional housing 340 having a control element 350 including a push button 354. The desired angle can be set by manually moving the housing 340 with respect to the driver tip/guide. The push button 354 can be compressed/released to set a pre-defined tension between the rod and the driver tip/guide. For example, the push button 354 can control multiple tension settings, wherein each depression of the push button 354 increases tension, and final push of the push button 354 completely releases tension.

Disclosed herein are methods for using the implant holder and guide device 200 and the driver 100, both individually and/or together. After the surgical site is prepared and disc material removed, the implant holder and guide device 200 can be used to insert the implant/spacer in the disc space. As outlined above, the detachable guide 230 is coupled to the rotatable driver shaft 210. For example, the proximal end/neck 243 of the guide 230 can be brought into contact with the collar 233. Rotation of the housing 240 causes the threaded interface 234 of the collar 233 to engage the corresponding interface 247 on the guide 230.

The implant 232 can then be coupled to the guide 230 (it is also contemplated that the implant 232 can be coupled to the guide 230 before the guide 230 is coupled to the driver shaft 210). As described above, projections 239 extending from the guide 230 are sized and configured to engage a corresponding opening in the implant 232. The implant 232 is secured to the guide 230 by further engagement between the driver shaft 210 and the guide 230/collar 233. As the driver shaft 210 engages the guide 230/collar 233, opposing halves of the guide body 231a, 231b move together/towards each other. As a result, the projection 239 and/or guide 230 compresses against the associated implant 232 and secures the implant 232 to the guide 230.

Just as the implant 232 can be coupled to the guide 230 before/after coupling with the driver shaft 210, likewise, a spacer/bone graft can be coupled to the implant 232 before or after the implant 232 is coupled to the guide 230. As illustrated in FIG. 14, for example, the implant 232 includes arms 235 that can expand/flex around the spacer/bone graft. Pressure applied by the arms 235 secures the spacer to the implant 232 and guide 230. Likewise, engagement features (teeth, grooves, barbs, etc.) included on the arms 235 can be included to secure the spacer to the arms 235.

With the spacer coupled to the implant holder and guide device 200, the spacer can be inserted into the disc space. Once the implant is fixed in a desired location within the patient, the detachable guide 230 can be removed from the implant 232. Removing the guide 230 from the patient, improves visibly and access to the surgical site for the fixation portion of the procedure. The guide 230 is removed from the implant 232 by manipulating/rotating the housing 240 (according to the various examples outlined herein). In one example, the detachable guide 230 is threadably engaged with the collar 233, and can be released by unscrewing the guide 230/collar 233 and allowing the opposing halves 231a, 231b of the guide 230 to release from the implant 232. It is also contemplated that the guide 230 (with or without the collar 233) will remain attached to the implant 232 during the fixation procedure. For example, the shaft 210 and housing 240 can be detached from the guide 230/collar 233 to improve visibility and access to the surgical site. It is further contemplated, that the guide 230, collar 233 and driver shaft 210 will remain coupled to the implant 232, only removing the housing 240, prior to the fixation procedure.

Once the user has removed the desired components from the implant holder and guide device 200 (e.g., only housing 240; housing 240 and driver shaft 210; housing 240, driver shaft 210 and collar 233; or housing 240, driver shaft 210, collar 233 and guide 230), the driver 100 can be used to place a screw or other fixation device into the spacer/implant 232, or directly into bone. Optionally, a screw is attached to the driver 100 through the interface 135 of the driver tip 130. As outlined above, the angle of the driver tip 130 with respect to the driver shaft 110 can be adjusted to accommodate the location of the implant and patient anatomy. For example, the user can (manually) adjust the angle of the driver tip 130 before coupling the interface 135/screw with the implant 232/guide 230. In another example, the user can insert the driver 100 into the surgical opening, couple the interface 135/screw with the implant 232/guide 230, and adjust the angle of the driver tip 130 by adjusting the angle of the driver shaft 110. Once the desired angle is achieved, the user can release the rod 120 and cause the rod 120 to engage the rotatable joint of the driver tip 130 thereby "locking" the angle of the driver tip 130 and preventing any further movement/change in angle between the driver tip 130 and the driver shaft 110. For example, as described above, where the rotatable joint comprises a ball-in-socket joint, the friction surface 122 of the rod 120 can engage the spherical head 132 of the driver tip 130. Frictional engagement between the friction surface 122 and the head 132 prevents any movement/change in angle between the driver tip 130 and the rod 120/driver shaft 110.

The "locked" screw/driver tip 130 is then inserted into the patient towards the guide 230. Fixing the angle of the driver tip 130 prior to insertion into the patient allows the user to identify a beneficial approach angle and minimize incision size and tissue trauma. Once the "locked" screw/driver tip 130 is positioned within the guide 230, the friction surface 122 of the rod 120 can be released from the head 132, i.e., the driver tip 130 can be "unlocked." The housing 140/rotatable driver shaft 110 can then be rotated to cause the screw to engage the implant 232/guide 230 and fix the implant 232/guide 230 to the spacer 205 and corresponding vertebral bodies. The guide 230 can be used to guide the screw into the proper location within the patient. Once the screw or other fixation device is properly affixed, the driver 100 can be removed from the patient.

As outlined above, the guide 230 can remain in the patient during the fixation procedure. Once the driver 100 has been used to fix the spacer/implant 232 in the disc space, the guide 230 can be removed from the patient by reattaching the shaft 210 of the implant holder and guide device 200 to the guide 230. Once the guide 230 is reattached to the implant holder and guide device 200, the user can release the guide 230 from the implant 232 as described above and remove the guide 230 from the patient by lifting the guide 230 through the surgical opening.

As outlined above, it is also contemplated that the driver 100 can act as a drill to prepare an opening for a corresponding bone screw. The angle of the driver tip 130/drill can be adjusted as described above with repsect to insertion of a bone screw.

The various components above may be made from PEEK, stainless steel, titanium, titanium alloy, ceramic, polyethylene, or any metallic or polymetric material. The various components may also include a TiN coating to limit wear and galling.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed:

1. A driver comprising:
   a driver shaft;
   a rod disposed within the driver shaft;
   a driver tip at a distal end of the driver shaft, the driver tip having a head that is coupled to a mating surface of the driver shaft at a ball-in-socket joint, wherein an angle of the driver tip relative to a longitudinal axis of the driver shaft is adjustable in at least two planes of direction to achieve an adjusted angle when the driver shaft is not rotating;
   a cross pin disposed in the head, and a second pin that extends through the cross pin, between opposite sides of the mating surface, and through a slot of the head, wherein the second pin guides movement between the head and the driver shaft;
   a housing that receives the driver shaft at a distal end thereof; and a control element disposed at a proximal end of the housing, the control element receiving a proximal end of the rod, wherein actuation of the control element engages the proximal end of the rod, causing a distal end of the rod to frictionally engage the joint, and secure the driver tip at the adjusted angle.

2. The driver of claim 1, wherein the head includes an interface extending therefrom adapted to engage a fastener.

3. The driver of claim 2, wherein the rod is adapted to frictionally engage the head, wherein the angle of the driver tip relative to a longitudinal axis of the driver shaft can be adjusted to a present angle and held at the preset angle through the frictional engagement of between the head and the rod.

4. The driver of claim 1, wherein an axial force is applied to the proximal end of the rod through engagement between the control element with the rod.

5. The driver of claim 1, wherein the housing is coupled to the driver shaft such that movement of the housing causes corresponding movement of the driver shaft and a resulting pivoting movement of the joint, thereby allowing the angle of the driver tip to change with respect to the driver shaft.

6. The driver of claim 1, wherein engagement between the rod and the control element fixes a position of the rod within the housing.

7. The driver of claim 1, wherein the rod is spring loaded within the housing.

8. The driver of claim 1, wherein the driver tip includes an interface extending therefrom adapted to engage a fastener, wherein the angle of the interface with respect to the rod can vary by up to about 180°.

9. The driver of claim 1, wherein the driver tip includes an interface extending therefrom adapted to engage a fastener, wherein the angle of the interface with respect to the rod can vary by about 45°.

10. The driver of claim 1, further comprising a mating sleeve coupling the driver shaft to the housing, the mating sleeve fixedly coupled to a proximal end of the driver shaft, wherein the driver shaft extends into a central channel of the mating sleeve, the proximal end of the driver shaft not extending beyond a proximal end of the mating sleeve.

11. The driver of claim 10, wherein the mating sleeve is disposed within an opening provided at the distal end of the housing, and the mating sleeve is removably coupled to the housing via engagement between threads provided on an interior surface of the housing and corresponding threads provided on an exterior surface of the mating sleeve.

12. The driver of claim 11, wherein the rod extends through the central channel of the mating sleeve and into the housing and is fixedly coupled to the control element.

13. The driver of claim 1, wherein the cross pin extends in a direction transverse to a longitudinal axis of the slot.

14. The driver of claim 1, wherein the driver tip includes an interface extending therefrom adapted to engage a fastener, wherein a sleeve extends over and around the interface, the sleeve including flexible arms sized and configured to flex and compress against the fastener as the interface engages a corresponding drive surface of the fastener.

15. The driver of claim 14, wherein the sleeve comprises a cylindrically-shaped band with a plurality of flexible arms extending from a proximal end of the band and a plurality of flexible arms extending from a distal end of the band.

16. The driver of claim 1, wherein the driver tip has a spherical head that is coupled to a domed mating surface of the driver shaft.

17. The driver of claim 1, wherein the driver shaft is rotatable.

\* \* \* \* \*